(12) United States Patent
Ishiwata

(10) Patent No.: US 9,770,313 B2
(45) Date of Patent: Sep. 26, 2017

(54) PROSTHESIS

(71) Applicant: NANTOH. CO., LTD, Numazu-shi, Shizuoka (JP)

(72) Inventor: Teruo Ishiwata, Numazu (JP)

(73) Assignee: NANTOH. CO., LTD, Numazu-Shi (JP)

( * ) Notice: Subject to any disclaimer, the term of this patent is extended or adjusted under 35 U.S.C. 154(b) by 0 days.

(21) Appl. No.: 14/772,225

(22) PCT Filed: Jul. 18, 2014

(86) PCT No.: PCT/JP2014/069154
§ 371 (c)(1),
(2) Date: Sep. 2, 2015

(87) PCT Pub. No.: WO2015/025656
PCT Pub. Date: Feb. 26, 2015

(65) Prior Publication Data
US 2016/0022391 A1    Jan. 28, 2016

(30) Foreign Application Priority Data

Aug. 20, 2013  (JP) .................................. 2013-170659

(51) Int. Cl.
*A61C 13/08* (2006.01)
*A61C 8/00* (2006.01)
(Continued)

(52) U.S. Cl.
CPC .......... *A61C 13/082* (2013.01); *A61C 8/0012* (2013.01); *A61C 13/0006* (2013.01);
(Continued)

(58) Field of Classification Search
CPC . A61C 13/082; A61C 13/083; A61C 13/0006; A61C 13/01; A61C 5/10;
(Continued)

(56) References Cited

U.S. PATENT DOCUMENTS

| 4,960,733 | A  | * | 10/1990 | Kasuga ................... A61L 27/12 501/10 |
| 2009/0087815 | A1 |  | 4/2009 | Oyama et al. |
| 2010/0236449 | A1 | * | 9/2010 | Hashimoto ............ A61K 6/033 106/35 |

FOREIGN PATENT DOCUMENTS

| JP | 6-293579 A | 10/1994 |
| JP | 10-1362 A | 1/1998 |

(Continued)

OTHER PUBLICATIONS

International Search Report dated Sep. 30, 2014, issued in counterpart application No. PCT/JP2014/069154 (5 pages).
(Continued)

*Primary Examiner* — Richard Chang
(74) *Attorney, Agent, or Firm* — Westerman, Hattori, Daniels & Adrian, LLP

(57) ABSTRACT

A prosthesis that contains zirconia and supplements a defective portion of a natural bone, and that is changed to a color approximate to that of the natural bone by a heat treatment after a γ-ray sterilization treatment. The color approximate to that of the natural bone has an L* value of 60 to 90, an a* value of −5 to 10, and a b* value of −5 to 10 in the L*a*b* color space. The highest temperature in the heat treatment is 100° C. to 300° C. The prosthesis is a fixture of a dental implant embedded into and bonded to a natural bone, an abutment, an implant crown, and the like.

17 Claims, 11 Drawing Sheets

(51) Int. Cl.
   *A61C 13/00* (2006.01)
   *A61C 13/01* (2006.01)
   *A61K 6/02* (2006.01)
   *A61L 2/08* (2006.01)
   *C04B 35/486* (2006.01)
   *A61K 6/00* (2006.01)
   *A61C 13/083* (2006.01)
   *A61F 2/28* (2006.01)

(52) U.S. Cl.
   CPC ............ *A61C 13/01* (2013.01); *A61C 13/083* (2013.01); *A61K 6/0044* (2013.01); *A61K 6/024* (2013.01); *A61L 2/081* (2013.01); *C04B 35/486* (2013.01); *A61C 2008/0046* (2013.01); *A61F 2/28* (2013.01); *A61F 2240/002* (2013.01); *A61L 2202/21* (2013.01); *C04B 2235/3244* (2013.01); *C04B 2235/604* (2013.01); *C04B 2235/9661* (2013.01)

(58) Field of Classification Search
   CPC .......... A61C 8/0012; A61C 2008/0046; A61K 6/0044; A61K 6/024; A61L 2/081; A61L 2202/21; C04B 35/486; C04B 2235/9661; A61F 2/28; A61F 2240/002
   See application file for complete search history.

(56) References Cited

FOREIGN PATENT DOCUMENTS

| | | |
|---|---|---|
| JP | 2000-191372 A | 7/2000 |
| JP | 2001-287987 A | 10/2001 |
| JP | 2004-59374 A | 2/2004 |
| JP | 2009-82171 A | 4/2009 |
| JP | 2013-193901 A | 9/2013 |
| JP | 2014-141388 A | 8/2014 |

OTHER PUBLICATIONS

Memorandum of Decision to Grant a Patent dated Sep. 18, 2015 issued in corresponding Japanese application No. 2013-170659, with English translation. (2 pages).

Decision to Grant a Patent dated Sep. 18, 2015 issued in corresponding Japanese application No. 2013-170659, with English translation. (5 pages).

Extended (Supplementary) European Search Report dated Jul. 13, 2016 issued in counterpart application No. 14838179.1 (6 pages).

Chinese Office Action dated Jul. 1, 2016, issued in counterpart Chinese aplication No. 201480024300.1. (5 pages).

* cited by examiner

PROSTHESIS

TECHNICAL FIELD

The present invention relates to a method for producing a prosthesis for supplementing a defective portion of a natural bone; for example, a dental implant that is embedded into the jaw bone when a tooth root of a permanent tooth is lost.

The present application claims priority based on the Japanese Patent Application No. 2013-170659 filed in Japan on Aug. 20, 2013, and the content thereof is incorporated herein by reference.

BACKGROUND ART

Implants that are embedded into the body are attracting attention as a kind of the prostheses that supplement a defective portion of a natural bone. In particular, a dental implant that is embedded into the jaw bone is attracting attention.

The dental implant is inserted into and fixed to a hole provided at the alveolar bone in a case where a tooth root of a permanent tooth has been lost due to dental caries or damage.

The dental implant is composed of a fixture (artificial tooth root) to be fixed to the alveolar bone, an abutment (support base) to be screwed to the fixture, and an implant crown (artificial crown) to be mounted on the abutment.

The implant crown is always exposed in the oral cavity. In a case where the implant crown is formed of zirconia, zirconia has a color different from that of a natural tooth (dark brown or pure white); therefore, the aesthetics in the oral cavity are compromised.

When the gingiva is retracted, the part of the fixture and abutment is exposed from the gingiva. Therefore, also in a case where the fixture and abutment are formed of zirconia, the aesthetics in the oral cavity are compromised as in a case of the implant crown.

In Patent Literature 1, a technique for coloring an abutment color to a color approximate to that of the gingiva (red) has been disclosed. Because the abutment is red in color, the decrease in oral cavity aesthetics can be prevented, even in a case where the gingiva is retracted, and the abutment is exposed.

CITATION LIST

Patent Literature

Patent Literature 1: Japanese Patent Application Laid-Open No. 2009-82171

SUMMARY OF INVENTION

Technical Problem

The technique of Patent Literature 1 is only intended for an abutment. The technique of Patent Literature 1 can be applied also to a fixture. However, when the technique of Patent Literature 1 is applied to an implant crown, the implant crown is tinted red; therefore, the aesthetics in the oral cavity are rather compromised.

The implant crown is desired to be colored to a color (white) approximate to that of the natural tooth of the wearer of the implant. A fixture and an abutment are also desired to be colored to a color approximate to that of the natural tooth.

In the technique of Patent Literature 1, the coloring is performed by the addition of a pigment to ceramic (a raw material) such as zirconia. However, an implant is embedded into the body, therefore, the adverse effect of the pigment on the human body is concerned. Therefore, it is desirable to color the implant to a color approximate to that of the natural tooth without using a coloring material such as a pigment.

An object of the present invention is to provide a method for producing a prosthesis colored to a color approximate to that of the natural bone without using a coloring material.

Solution to Problem

The first embodiment of the present invention is characterized by a method for producing a prosthesis containing zirconia and supplementing a defective portion of a natural bone, in which the prosthesis color is changed to a color approximate to that of the natural bone by a heat treatment after a γ-ray sterilization treatment.

The second embodiment of the present invention is characterized in that in the first embodiment, the color approximate to that of the natural bone has an $L^*$ value of 60 to 90, an $a^*$ value of −5 to 10, and a $b^*$ value of −5 to 10 in the $L^*a^*b^*$ color space.

The third embodiment of the present invention is characterized in that in the first and the second embodiments, the heat treatment has a highest temperature of 100° C. to 300° C.

The fourth embodiment of the present invention is characterized in that in any one of the first to the third embodiments, the prosthesis is an implant embedded into and bonded to a natural bone.

The fifth embodiment of the present invention is characterized in that in the fourth embodiment, the prosthesis is a dental implant.

The sixth embodiment of the present invention is characterized in that in the fifth embodiment, the prosthesis is a fixture of a dental implant.

The seventh embodiment of the present invention is characterized in that in the fifth embodiment, the prosthesis is an abutment of a dental implant.

The eighth embodiment of the present invention is characterized in that in the fifth embodiment, the prosthesis is an implant crown of a dental implant.

The ninth embodiment of the present invention is characterized in that in any one of the first to the third embodiments, the prosthesis is a filling to be embedded into a defective portion of a natural tooth.

The tenth embodiment of the present invention is characterized in that in any one of the first to the third embodiments, the prosthesis is a post crown to be mounted on a tooth root.

The eleventh embodiment of the present invention is characterized in that in any one of the first to the third embodiments, the prosthesis is a bridge composed of an artificial tooth that serves as a substitute for a defected natural tooth, and a crown covering a natural tooth that is to be adjacent to the artificial tooth.

The twelfth embodiment of the present invention is characterized in that in any one of the first to the third embodiments, the prosthesis is a plate denture.

The thirteenth embodiment of the present invention is characterized in that in any one of the first to the third embodiments, the prosthesis is an artificial bone.

The fourteenth embodiment of the present invention is characterized in that in any one of the first to the third embodiments, the prosthesis is a bone prosthetic material.

Advantageous Effects of Invention

The present invention can achieve a prosthesis colored to a color approximate to that of the natural bone without using a coloring material.

DESCRIPTION OF EMBODIMENTS

The embodiments of the present invention will be described with reference to drawings. Various sizes and the like shown in the following description are only examples.

Figure 1:
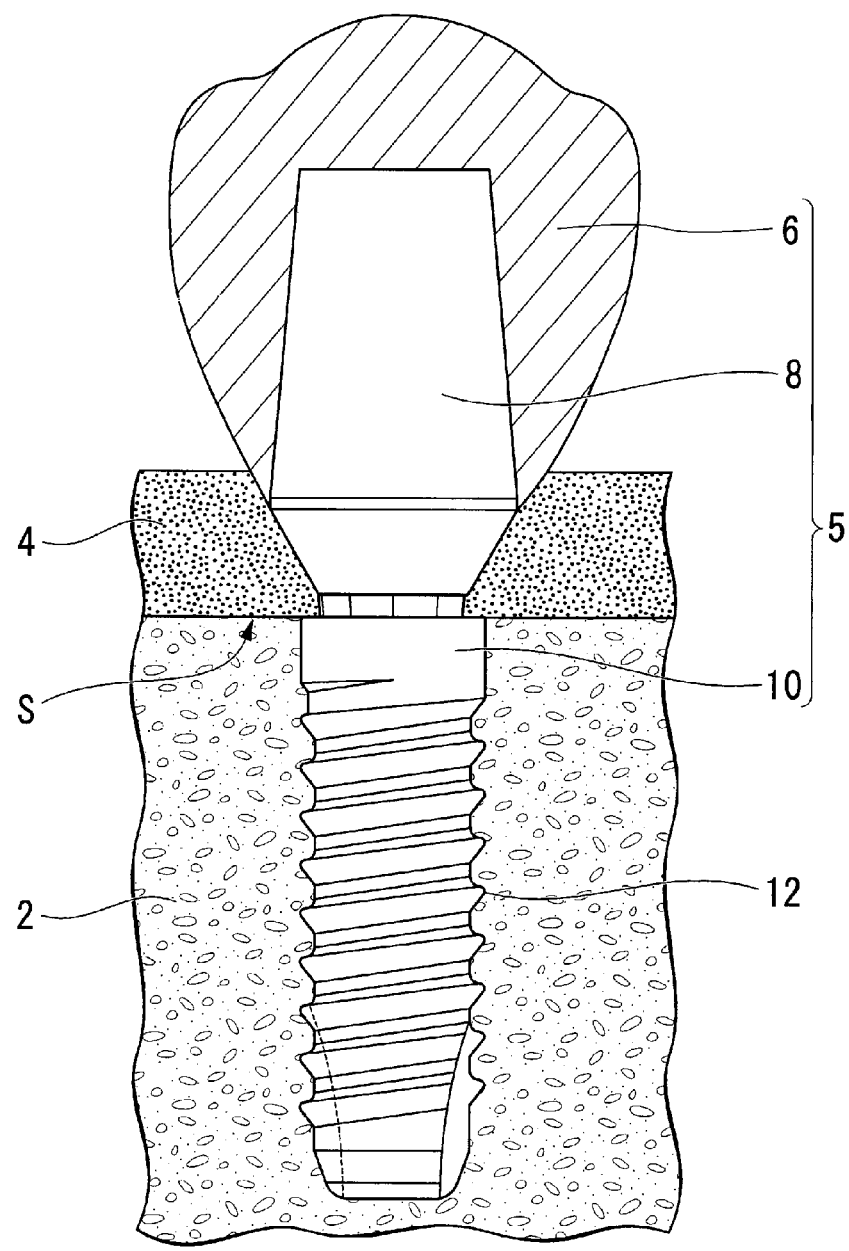
FIG. 1 is a diagram showing a dental implant 5 according to the embodiment of the present invention.

FIG. 1 is a diagram showing a dental implant 5 according to the embodiment of the present invention.

A dental implant (implant, prosthesis) 5 is fixed to an alveolar bone (natural bone) 2.

The implant 5 includes a fixture 10 to be fixed to an alveolar bone 2, an abutment body 8 that is detachable from the fixture 10, and an artificial crown 6 to be mounted on the abutment 8.

A male screw 12 is formed on the outer peripheral surface of the fixture 10. By screwing the male screw 12 into a hole formed in an alveolar bone 2, the fixture 10 is fixed to the alveolar bone 2.

The artificial crown 6 is mounted on the outer peripheral surface of the abutment (prosthesis) 8 by using an adhesive or the like.

An artificial crown (prosthesis) 6 is called an upper structure or an implant denture.

A contact section S between the fixture 10 and the abutment 8 is covered by a gum 4 or the alveolar bone 2. However, when the gum 4 is retracted, the contact section S between the fixture 10 and the abutment 8 is exposed in the oral cavity.

The artificial crown 6 is always exposed in the oral cavity.

The artificial crown 6, the abutment 8, and the fixture 10 are formed of ceramic containing zirconia as a main component.

The artificial crown 6, the abutment 8, and the fixture 10 are respectively produced through the following process A.

[The First Process A1: Press Sintering Treatment Process (Forming Process)]

Powders of zirconia (PXA-200 type manufactured by TOSOH CORPORATION, or the like) are put into a mold having the form of an artificial crown 6 or the like with a cavity, and press molded. After that, the press-molded article is sintered at a temperature of, for example, 1500° C. or more.

As a result, a formed article of an artificial crown 6, an abutment 8, and a fixture 10 is obtained.

[The Second Process A2: γ-Ray Sterilization Treatment Process (Dark-Browning Process)]

By the irradiation of the formed article of an artificial crown 6, an abutment 8, and a fixture 10 with a γ-ray, the formed article is sterilized. Irradiation is performed with a γ-ray in a dose of, for example, 25 kGy or more.

As a result, the formed article of an artificial crown 6, an abutment 8, and a fixture 10 turns dark brown. The formed article of an artificial crown 6, an abutment 8, and a fixture 10 turns dark brown not only on the outside surface but also on the inside.

[The Third Process A3: Heat Treatment Process (Whitening Process)]

A formed article of an artificial crown 6, an abutment 8, and a fixture 10 is heated to 100° C. to 300° C. The highest temperature may be 100° C. to 300° C. The heating time, the retention time, and the like can be set arbitrarily.

As a result, the dark-brown formed article is whitened, and colored to a color approximate to that of the natural tooth. That is, a prosthesis colored to a color approximate to that of the natural tooth (artificial crown 6, abutment 8, and fixture 10) is obtained.

The artificial crown 6, the abutment 8, and the fixture 10 are colored to a color approximate to that of the natural tooth not only on the outside surface but also on the inside.

Table 1 is a table showing colorimetric results of the prostheses S1 to S13 formed through the above-described production processes A (A1 to A3).

TABLE 1

|  |  | Lightness | Hue | | Saturation |
|---|---|---|---|---|---|
|  |  | L* (D65) | a* (D65) | b* (D65) | SQRT ($a^{*2} + b^{*2}$) |
| Specimens | S1 | 65.61 | 5.48 | 2.52 | 6.03 |
|  | S2 | 75.23 | 2.39 | 5.88 | 6.35 |
|  | S3 | 77.47 | 1.73 | 6.37 | 6.60 |
|  | S4 | 80.29 | 0.63 | 6.61 | 6.64 |
|  | S5 | 81.25 | 0.32 | 6.29 | 6.30 |
|  | S6 | 81.60 | −0.10 | 6.16 | 6.16 |
|  | S7 | 83.10 | −0.43 | 5.98 | 6.00 |
|  | S8 | 83.35 | −0.62 | 5.83 | 5.86 |
|  | S9 | 84.18 | −1.06 | 5.08 | 5.19 |
|  | S10 | 84.58 | −1.32 | 4.36 | 4.56 |
|  | S11 | 84.98 | −1.56 | 3.71 | 4.02 |
|  | S12 | 88.22 | −1.48 | −0.04 | 1.48 |
|  | S13 | 87.94 | −1.37 | −0.08 | 1.37 |
| Comparative examples | S21 | 86.88 | −1.25 | −0.74 | 1.45 |
|  | S22 | 45.32 | 6.07 | −0.17 | 6.07 |
|  | S23 | 63.99 | −1.11 | 7.77 | 7.85 |

Figure 2:
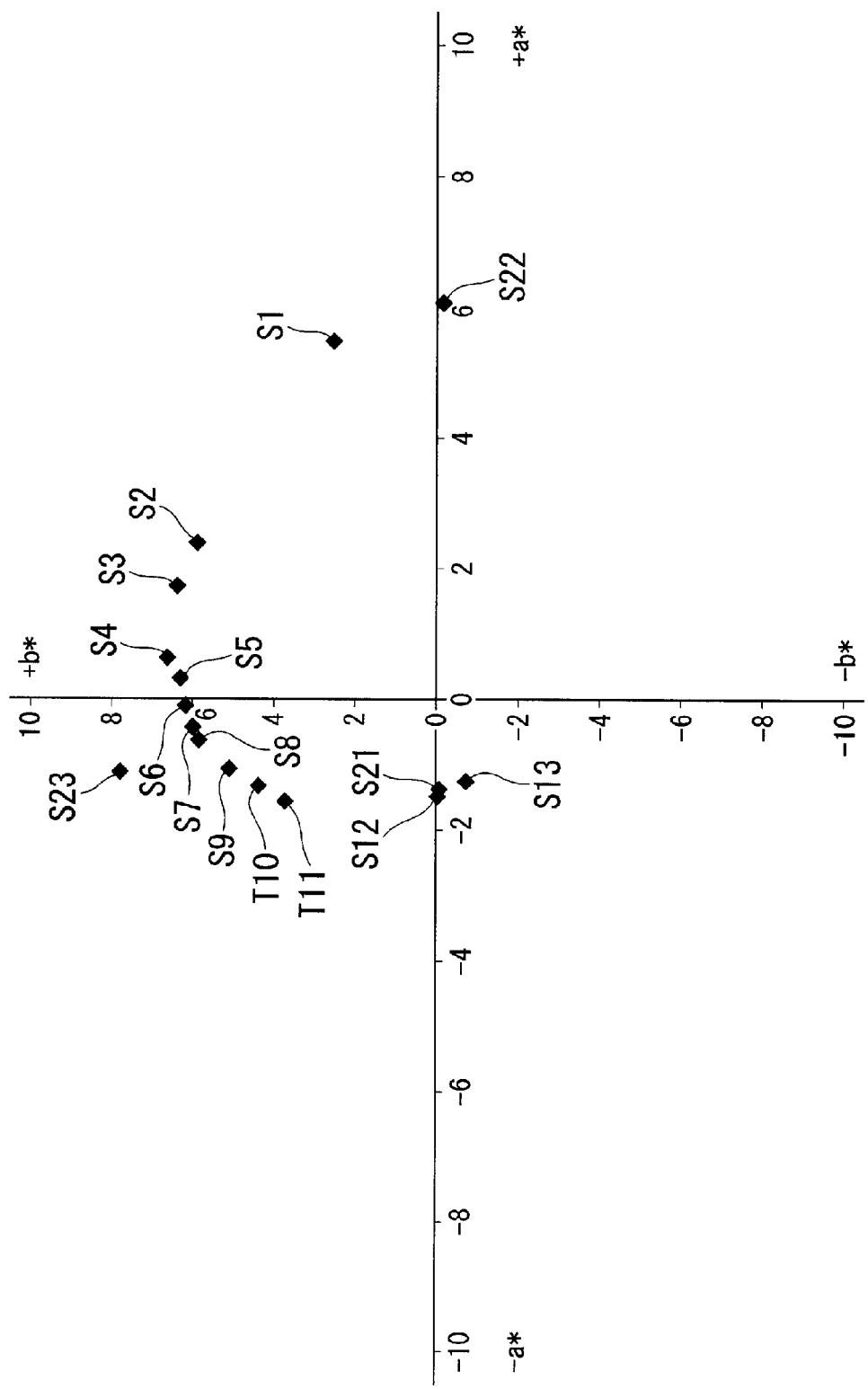
FIG. 2 is a chart showing colorimetric results (hue in the L*a*b* color space) of prostheses S1 to S13.

FIG. 2 is a chart showing colorimetric results (hue in the L*a*b* color space) of prostheses S1 to S13.

Figure 3:
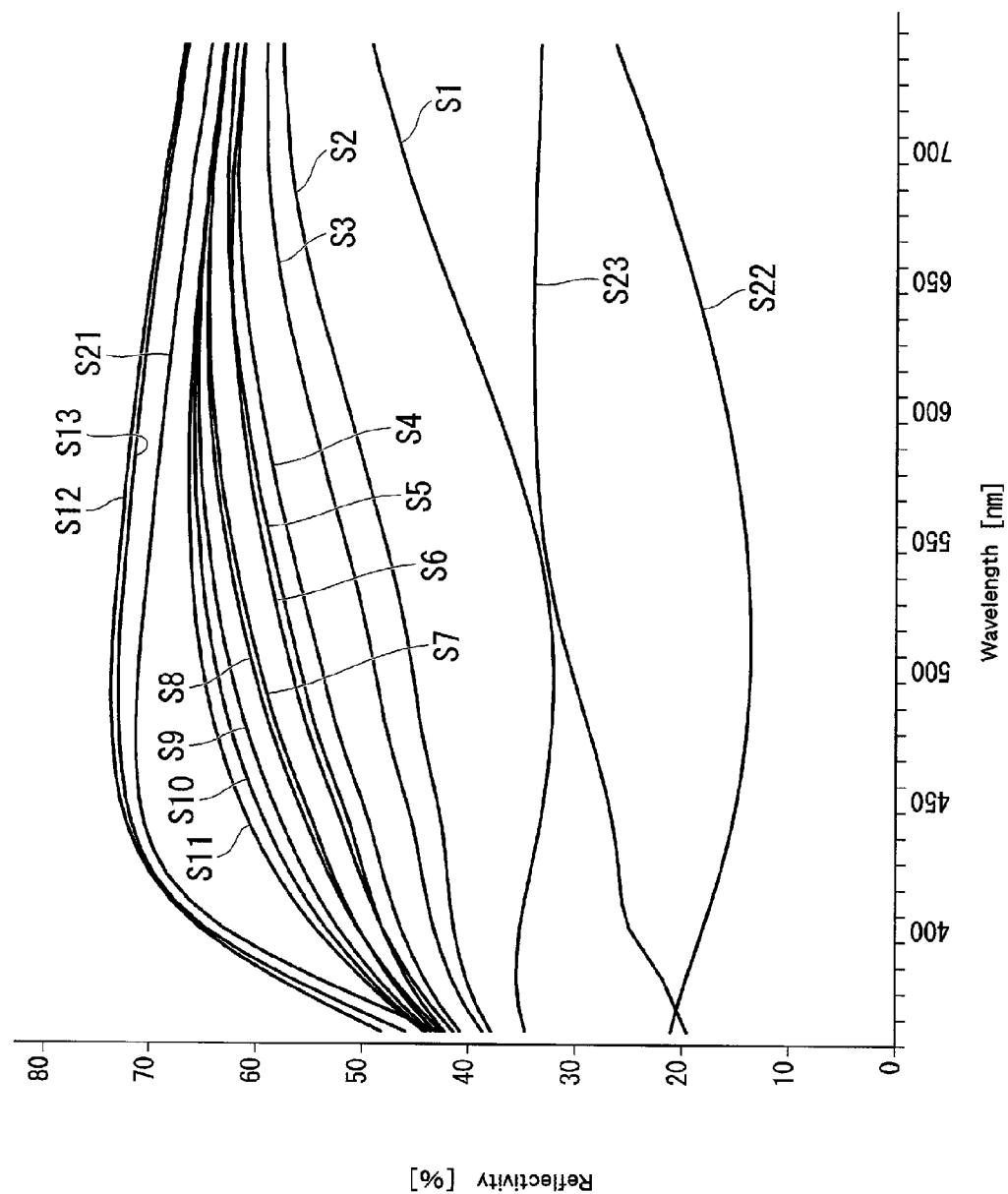
FIG. 3 is a chart showing colorimetric results (wavelength and reflectivity) of prostheses S1 to S13.

FIG. 3 is a chart showing colorimetric results (wavelength and reflectivity) of prostheses S1 to S13.

Color system: Lab color system (CIE 1976 (L*, a*, and b*) color space (CIELAB), JIS Z 8729)

Spectrophotometer: CM-1000 manufactured by KONICA MINOLTA, INC. (former Minolta Camera Co., Ltd.)

Materials of prostheses S1 to S13, and comparative examples S21 and S22: PXA-233P manufactured by TOSOH CORPORATION Prosthesis S1: the highest temperature is set to 100° C. in the third process A3.

Prosthesis S2: the highest temperature is set to 110° C. in the third process A3.

Prosthesis S3: the highest temperature is set to 120° C. in the third process A3.

Prosthesis S4: the highest temperature is set to 130° C. in the third process A3.

Prosthesis S5: the highest temperature is set to 140° C. in the third process A3.

Prosthesis S6: the highest temperature is set to 150° C. in the third process A3.

Prosthesis S7: the highest temperature is set to 160° C. in the third process A3.

Prosthesis S8: the highest temperature is set to 170° C. in the third process A3.

Prosthesis S9: the highest temperature is set to 180° C. in the third process A3.

Prosthesis S10: the highest temperature is set to 190° C. in the third process A3.

Prosthesis S11: the highest temperature is set to 200° C. in the third process A3.

Prosthesis S12: the highest temperature is set to 250° C. in the third process A3.

Prosthesis S13: the highest temperature is set to 300° C. in the third process A3.

Comparative example S21: passed through the first process A1 (omitted the second process A2 and the third process A3).

Comparative example S22: passed through the first process A1 and the second process A2 (omitted the third process A3).

Comparative example S23: a conventional artificial tooth (CEREC VITABLOCS MarkII manufactured by VITA).

The prostheses S1 to S13 are changed to a color approximate to that of the natural bone by a heat treatment (the third process A3) after a γ-ray sterilization treatment (the second process A2). The highest temperature in the heat treatment (the third process A3) is 100° C. to 300° C.

As shown in FIG. 2, the color approximate to that of the natural bone has an L* value of 60 to 90, an a* value of −5 to 10, and a b* value of −5 to 10 in the L*a*b* color space. Specifically, the L* value is 65 to 89, the a* value is −2 to 6, and the b* value is −1 to 8.

Prostheses S1 to S13 are whiter than the comparative example S22 that is dark brown, and browner than the comparative example S21 that is pure white. Therefore, the prostheses S1 to S13 are changed to a color approximate to that of the natural bone in the same manner as in the comparative example S23.

As shown in FIG. 3, prostheses S1 to S13 have higher reflectivity than that of the comparative example S23, but have a waveform shape approximate to that of the comparative example S23. Prostheses S1 to S13 have a waveform shape approximate to that of the comparative example S23, and are therefore recognized to be changed to a color approximate to that of the comparative example S23 (color approximate to that of the natural bone).

As described above, it was confirmed that prostheses S1 to S13 were colored to a color approximate to that of the natural bone (the same color as that of the comparative example S23). In particular, by setting the highest temperature in a heat treatment (the third process A3) to 100° C. to 300° C., prostheses S1 to S13 having a color approximate to that of the natural tooth of a wearer were obtained.

Therefore, since an artificial crown 6, an abutment 8, and a fixture 10 can be colored to a color approximate to that of the natural bone, the aesthetics in the oral cavity are not compromised. Even in a case where the artificial crown 6 and the like are worn, the inside is also colored to a color approximate to that of the natural bone; therefore, the aesthetics in the oral cavity are not compromised.

The artificial crown 6, the abutment 8, and the fixture 10 can also be produced through the following process B.

[The First Process B1: Press Sintering Treatment Process (Forming process)]

Powders of zirconia (PXA-200 type manufactured by TOSOH CORPORATION, or the like) are put into a mold having the same shape as that of an artificial crown 6 or the like with a cavity, and press molded. After that, the press-molded article is sintered at a temperature of, for example, 1500° C. or more.

As a result, a formed article of an artificial crown 6, an abutment 8, and a fixture 10 is obtained.

The first process B1 is the same process as that of the first process A1.

[The Second Process B2: Surface Treatment Process (Laser Processing Process)]

By the irradiation of the formed article of an artificial crown 6, an abutment 8, and a fixture 10 with a laser beam, the surface of the formed article is roughened.

As the laser beam, a Nd: YAG laser or YVO4 laser is used. For example, a fundamental wave of a Nd: YAG laser or YVO4 laser (solid-state laser: wavelength 1064 nm, and fiber laser: 1090 nm) can be used. The beam diameter (diameter) of the laser beam is, for example, 5 to 50 μm.

[The Third Process B3: High Temperature Heat Treatment Process (Color Restoration Process)]

A formed article of an artificial crown 6, an abutment 8, and a fixture 10 is heated to 700° C. The heating time, the retention time, and the like can be set arbitrarily.

As a result, the changed (dark-brown) formed article is whitened by the irradiation with a laser beam. The artificial crown 6, the abutment 8, and the fixture 10 are whitened not only on the outside surface but also on the inside.

[The Fourth Process B4: γ-Ray Sterilization Treatment Process (Dark-Browning Process)]

By the irradiation of the formed article of an artificial crown 6, an abutment 8, and a fixture 10 with a γ-ray, the formed article is sterilized. Irradiation with a γ-ray in a dose of, for example, 25 kGy or more is performed.

As a result, a formed article of an artificial crown 6, an abutment 8, and a fixture 10 turns dark brown. The formed article of an artificial crown 6, an abutment 8, and a fixture 10 turns dark brown not only on the outside surface but also on the inside.

The fourth process B4 is the same process as that of the second process A2.

[The Fifth Process B5: Heat Treatment Process (Whitening Process)]

The formed article of an artificial crown 6, an abutment 8, and a fixture 10 is heated to 100° C. to 300° C. The highest temperature may be 100° C. to 300° C. The heating time, the retention time, and the like can be set arbitrarily.

As a result, the dark-brown formed article is whitened, and colored to a color approximate to that of the natural tooth. That is, a prosthesis colored to a color approximate to that of the natural tooth (artificial crown 6, abutment 8, and fixture 10) is obtained.

The artificial crown 6, the abutment 8, and the fixture 10 are colored to a color approximate to that of the natural tooth not only on the outside surface but also in the inside.

The fifth process B5 is the same process as that of the third process A3.

Table 2 is a table showing colorimetric results of the prostheses T1 to T13 formed through the above-described production processes B (B1 to B5).

TABLE 2

|  |  | Lightness | Hue | | Saturation |
|---|---|---|---|---|---|
|  |  | L* (D65) | a* (D65) | b* (D65) | SQRT (a*² + b*²) |
| Specimens | T1 | 74.15 | 2.71 | 0.03 | 2.71 |
|  | T2 | 80.81 | 1.28 | 3.24 | 3.48 |
|  | T3 | 83.92 | −0.37 | 4.18 | 4.20 |
|  | T4 | 84.99 | −0.90 | 4.45 | 4.54 |
|  | T5 | 85.75 | −1.01 | 4.61 | 4.72 |
|  | T6 | 85.86 | −1.29 | 4.14 | 4.34 |
|  | T7 | 86.36 | −1.37 | 3.89 | 4.12 |
|  | T8 | 87.19 | −1.62 | 4.10 | 4.41 |
|  | T9 | 86.71 | −1.71 | 3.31 | 3.73 |
|  | T10 | 87.51 | −1.74 | 3.23 | 3.67 |
|  | T11 | 88.13 | −1.75 | 2.61 | 3.14 |
|  | T12 | 88.07 | −1.25 | −0.41 | 1.32 |
|  | T13 | 88.04 | −1.12 | −0.08 | 1.12 |
| Comparative | T21 | 68.70 | 3.30 | 3.14 | 4.56 |
| examples | T22 | 87.92 | −1.20 | −0.42 | 1.27 |
|  | T23 | 66.04 | 1.88 | −1.94 | 2.70 |
|  | T24 | 63.99 | −1.11 | 7.77 | 7.85 |

Figure 4:
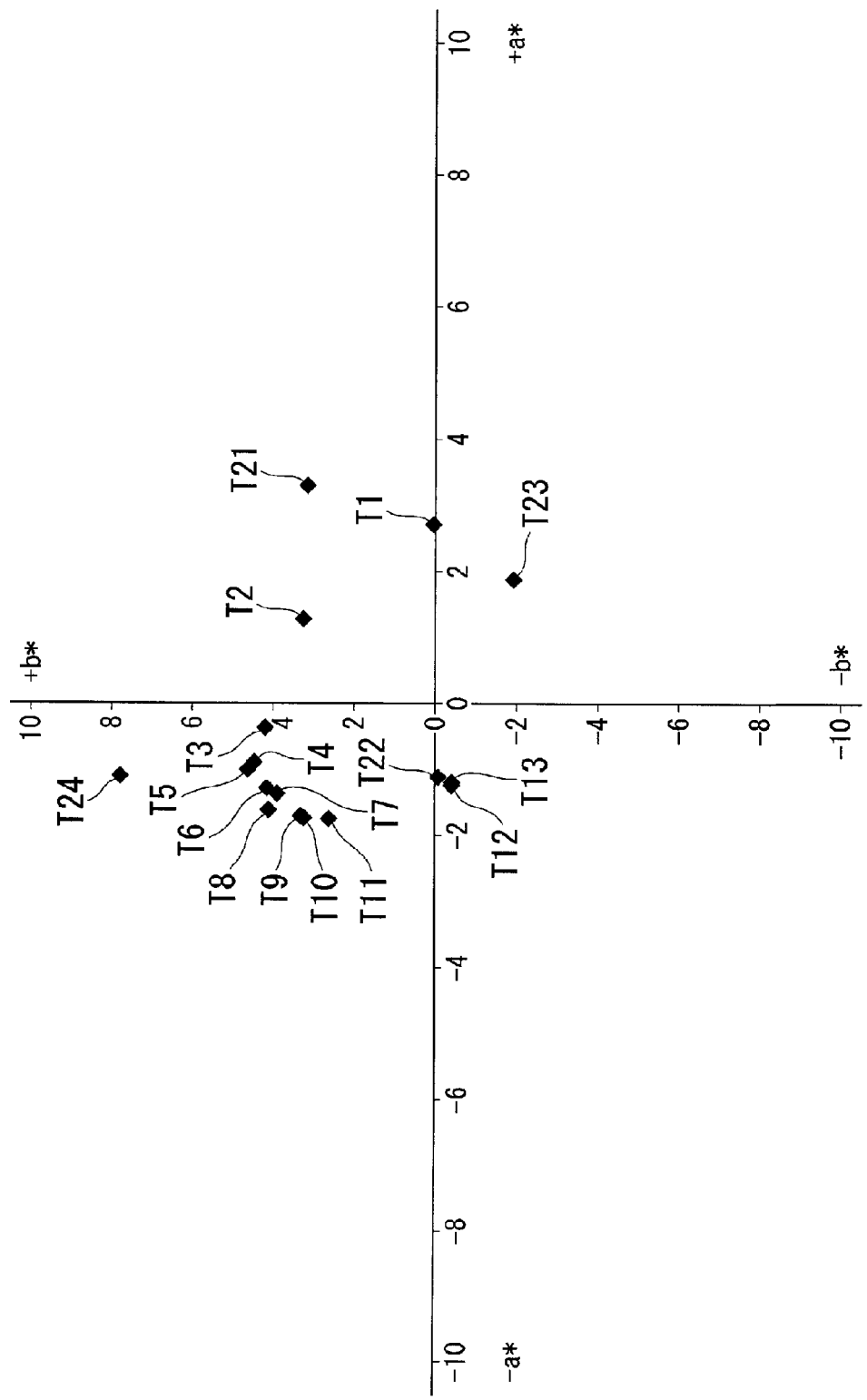
FIG. 4 is a chart showing colorimetric results (hue in the L*a*b* color space) of prostheses T1 to T13.

FIG. 4 is a chart showing colorimetric results (hue in the L*a*b* color space) of prostheses T1 to T13.

Figure 5:
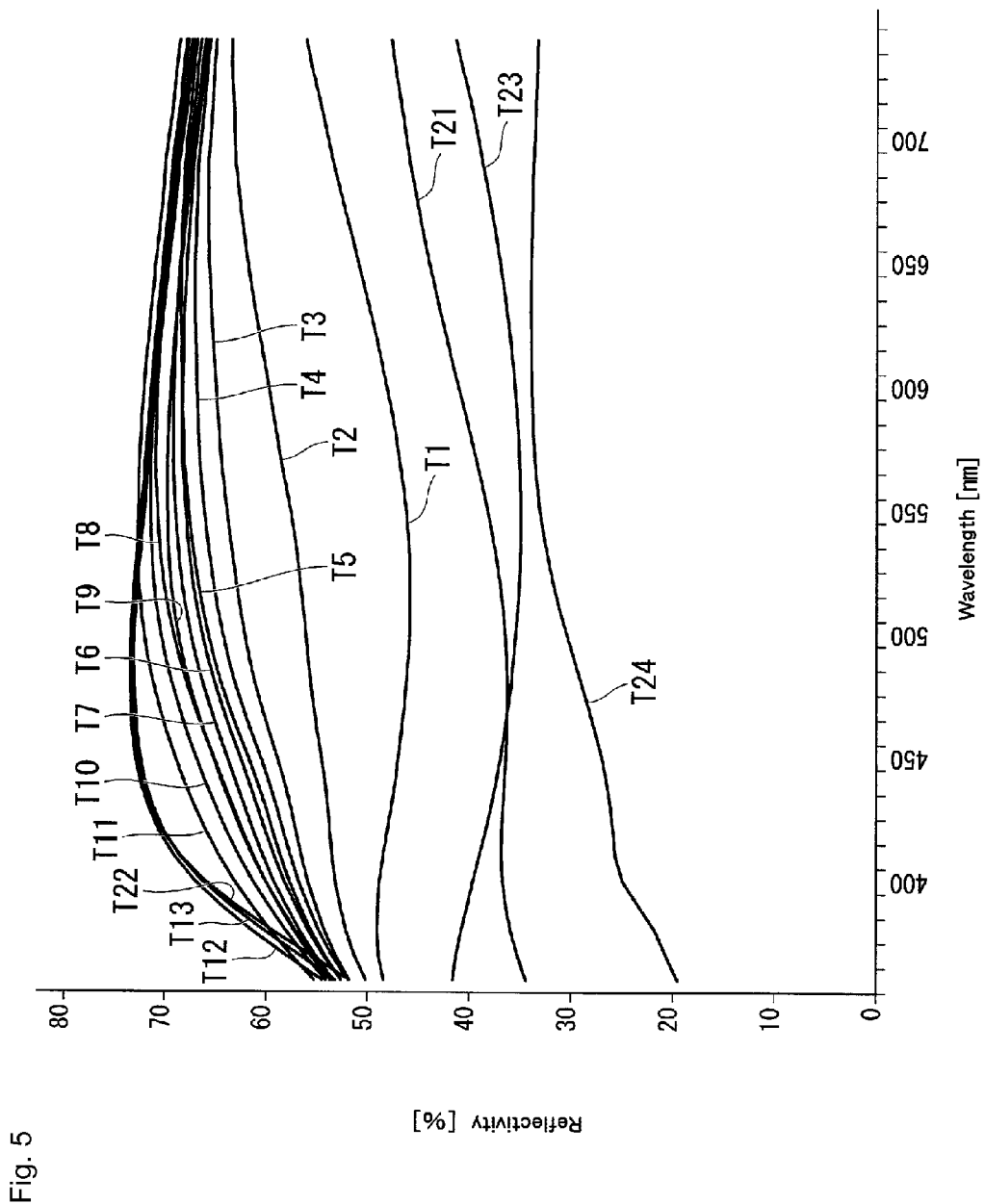
FIG. 5 is a chart showing colorimetric results (wavelength and reflectivity) of prostheses T1 to T13.

FIG. 5 is a chart showing colorimetric results (wavelength and reflectivity) of prostheses T1 to T13.

Color system: Lab color system (CIE 1976 (L*, a*, and b*) color space (CIELAB), JIS Z 8729)

Spectrophotometer: CM-1000 manufactured by KONICA MINOLTA, INC. (former Minolta Camera Co., Ltd.)

Materials of prostheses T1 to T13, and comparative examples T21 to T23: PXA-233P manufactured by TOSOH CORPORATION Prosthesis T1: the highest temperature is set to 100° C. in the fifth process B5.

Prosthesis T2: the highest temperature is set to 110° C. in the fifth process B5.

Prosthesis T3: the highest temperature is set to 120° C. in the fifth process B5.

Prosthesis T4: the highest temperature is set to 130° C. in the fifth process B5.

Prosthesis T5: the highest temperature is set to 140° C. in the fifth process B5.

Prosthesis T6: the highest temperature is set to 150° C. in the fifth process B5.

Prosthesis T7: the highest temperature is set to 160° C. in the fifth process B5.

Prosthesis T8: the highest temperature is set to 170° C. in the fifth process B5.

Prosthesis T9: the highest temperature is set to 180° C. in the fifth process B5.

Prosthesis T10: the highest temperature is set to 190° C. in the fifth process B5.

Prosthesis T11: the highest temperature is set to 200° C. in the fifth process B5.

Prosthesis T12: the highest temperature is set to 250° C. in the fifth process B5.

Prosthesis T13: the highest temperature is set to 300° C. in the fifth process B5.

Comparative example T21: passed through the first process B1 and the second process B2 (omitted the third process B3 to the fifth process B5).

Comparative example T22: passed through the first process B1 to the third process B3 (omitted the fourth process B4 and the fifth process B5).

Comparative example T23: passed through the first process B1 to the fourth process B4 (omitted the fifth process B5).

Comparative example T24: a conventional artificial tooth (CEREC VITABLOCS MarkII manufactured by VITA). The comparative example T24 is the same as the comparative example S23.

The prostheses T1 to T13 are changed to a color approximate to that of the natural bone by a heat treatment (the fifth process B5) after a γ-ray sterilization treatment (the fourth process B4). The highest temperature in the heat treatment (the fifth process B5) is 100° C. to 300° C.

As shown in FIG. 4, the color approximate to that of the natural bone has an L* value of 60 to 90, an a* value of −5 to 10, and a b* value of −5 to 10 in the L*a*b* color space. Specifically, the L* value is 65 to 89, the a* value is −2 to 6, and the b* value is −1 to 8.

Prostheses T1 to T13 are whiter than the comparative examples T21 and T23 that are dark brown, and browner than the comparative example T22 that is pure white. Therefore, the prostheses S1 to S13 are changed to a color approximate to that of the natural bone in the same manner as in the comparative example T24.

As shown in FIG. 5, the prostheses T1 to T13 have higher reflectivity than that of the comparative example T24, but have a waveform shape approximate to that of the comparative example T24. The prostheses T1 to T13 have a waveform shape approximate to that of the comparative example T24, and are therefore recognized to have been changed to a color approximate to that of the comparative example T24 (color approximate to that of the natural bone).

As described above, it was confirmed that prostheses T1 to T13 are colored to a color approximate to that of the natural bone (the same color as that of the comparative example T24). In particular, by setting the highest temperature in a heat treatment (the fifth process B5) to 100° C. to 300° C., prostheses T1 to T13 having color approximate to that of the natural tooth of a wearer were obtained.

Therefore, since an artificial crown 6, an abutment 8, and a fixture 10 can be colored to a color approximate to that of the natural bone, the aesthetics in the oral cavity are not compromised. Even in a case where the artificial crown 6, and the like are worn, the inside is also colored to a color approximate to that of the natural bone; therefore, the aesthetics in the oral cavity are not compromised.

Figure 6:
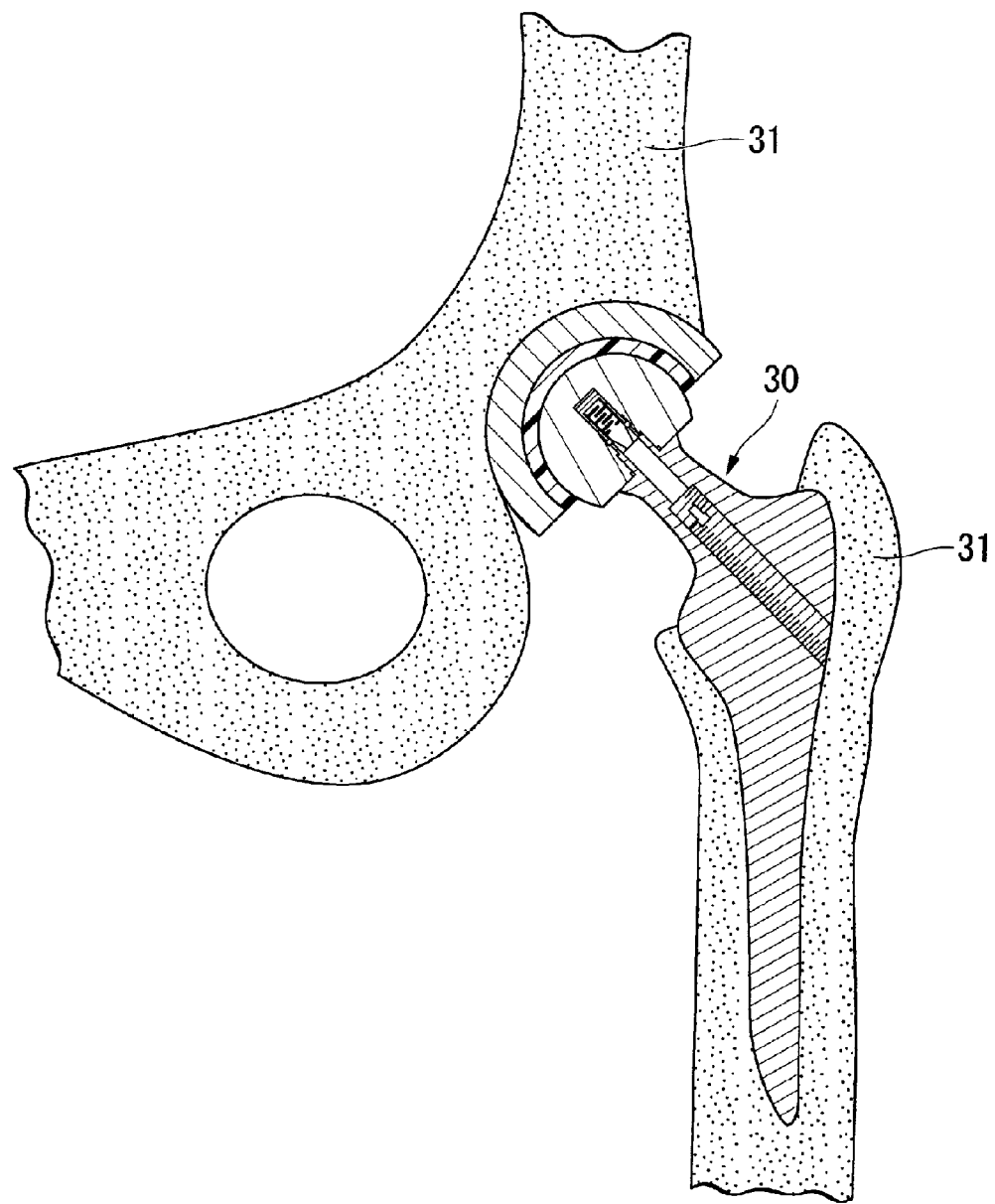
FIG. 6 is a diagram showing a surgical implant 30 according to the embodiment of the present invention.

FIG. 6 is a diagram showing a surgical implant 30 according to the embodiment of the present invention.

The prosthesis may be a surgical implant 30. The surgical implant (implant, prosthesis) 30 is embedded into a natural bone 31 that has been broken or the like. The surgical implant 30 is also used for fixing a natural bone that has been broken or the like.

A heat treatment (the third process A3, or the fifth process B5) is also performed in the production process of a surgical implant 30, after a γ-ray sterilization treatment (the second process A2, or the fourth process B4).

Figure 7:
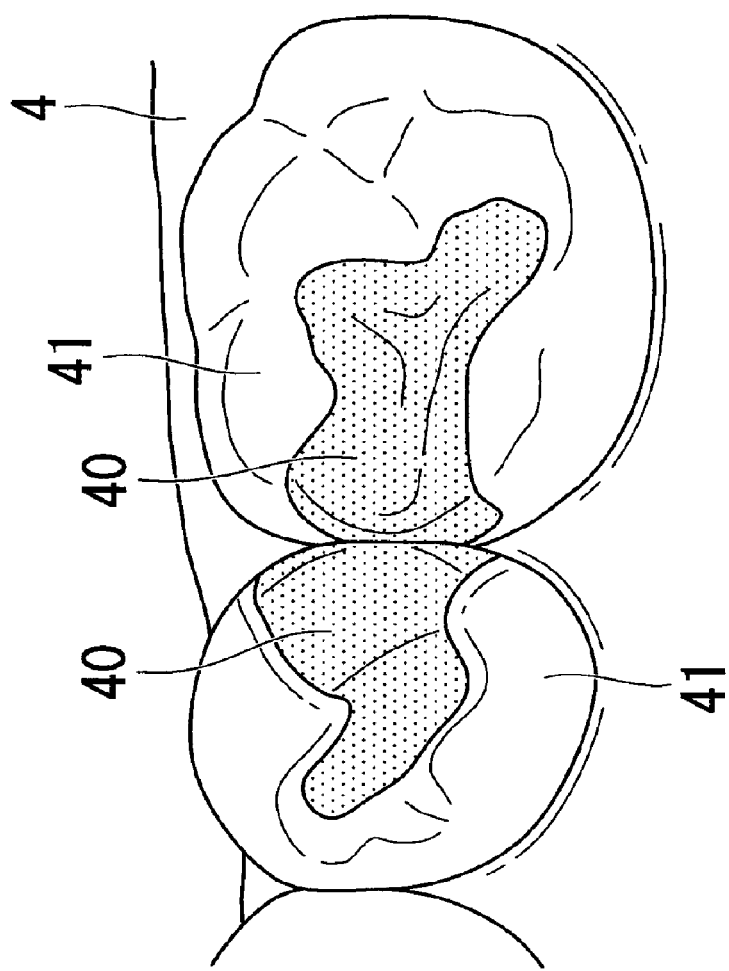
FIG. 7 is a diagram showing a filling 40 according to the embodiment of the present invention.

FIG. 7 is a diagram showing a filling 40 according to the embodiment of the present invention.

The prosthesis of the present invention may be a filling 40 (inlay, filling). The filling (prosthesis) 40 is embedded into a defective portion of a natural tooth (natural bone) 41.

A heat treatment (the third process A3, or the fifth process B5) is also performed in the production process of a filling 40, after a γ-ray sterilization treatment (the second process A2, or the fourth process B4).

Figure 8:
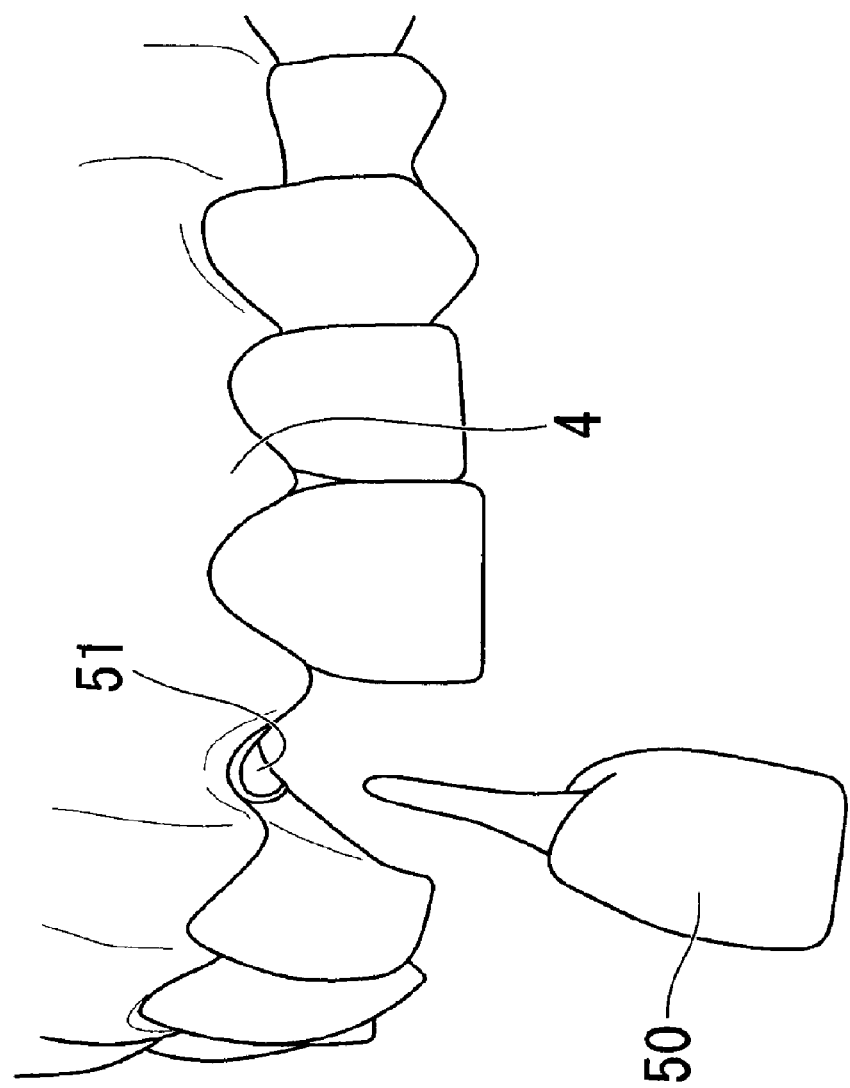
FIG. 8 is a diagram showing a post crown 50 according to the embodiment of the present invention.

FIG. 8 is a diagram showing a post crown 50 according to the embodiment of the present invention.

The prosthesis of the present invention may be a post crown 50. The post crown (prosthesis) 50 is mounted on a tooth root (natural bone).

A heat treatment (the third process A3, or the fifth process B5) is also performed in the production process of a post crown 50, after a γ-ray sterilization treatment (the second process A2, or the fourth process B4).

Figure 9:
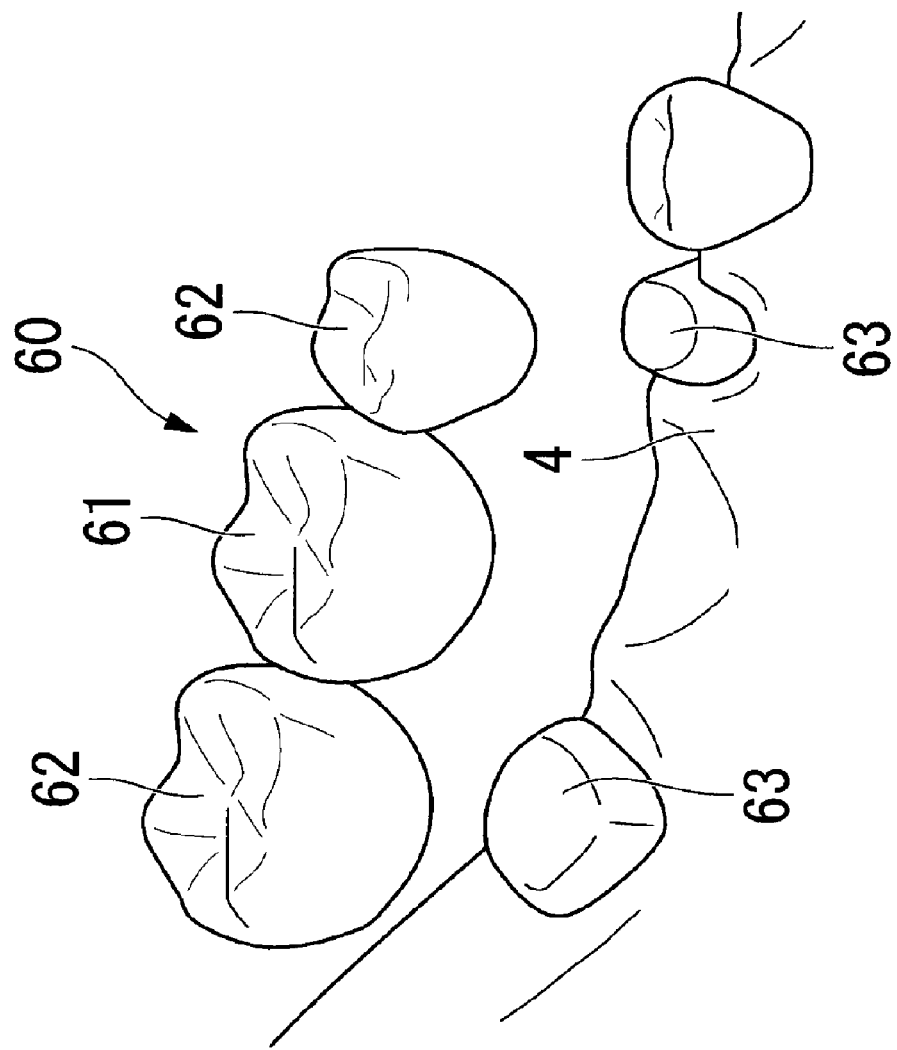
FIG. 9 is a diagram showing a bridge 60 according to the embodiment of the present invention.

FIG. 9 is a diagram showing a bridge 60 according to the embodiment of the present invention.

The prosthesis of the present invention may be a bridge 60 (fixed partial denture, or crown bridge denture). The bridge (prosthesis) 60 is composed of an artificial tooth 61 (dummy, pontic) that serves as a substitute for a defective natural tooth, and a crown 62 covering a natural tooth 63 (abutment tooth) that is to be adjacent to the artificial tooth 61.

A heat treatment (the third process A3, or the fifth process B5) is also performed in the production process of a bridge 60, after a γ-ray sterilization treatment (the second process A2, or the fourth process B4).

Figure 10:
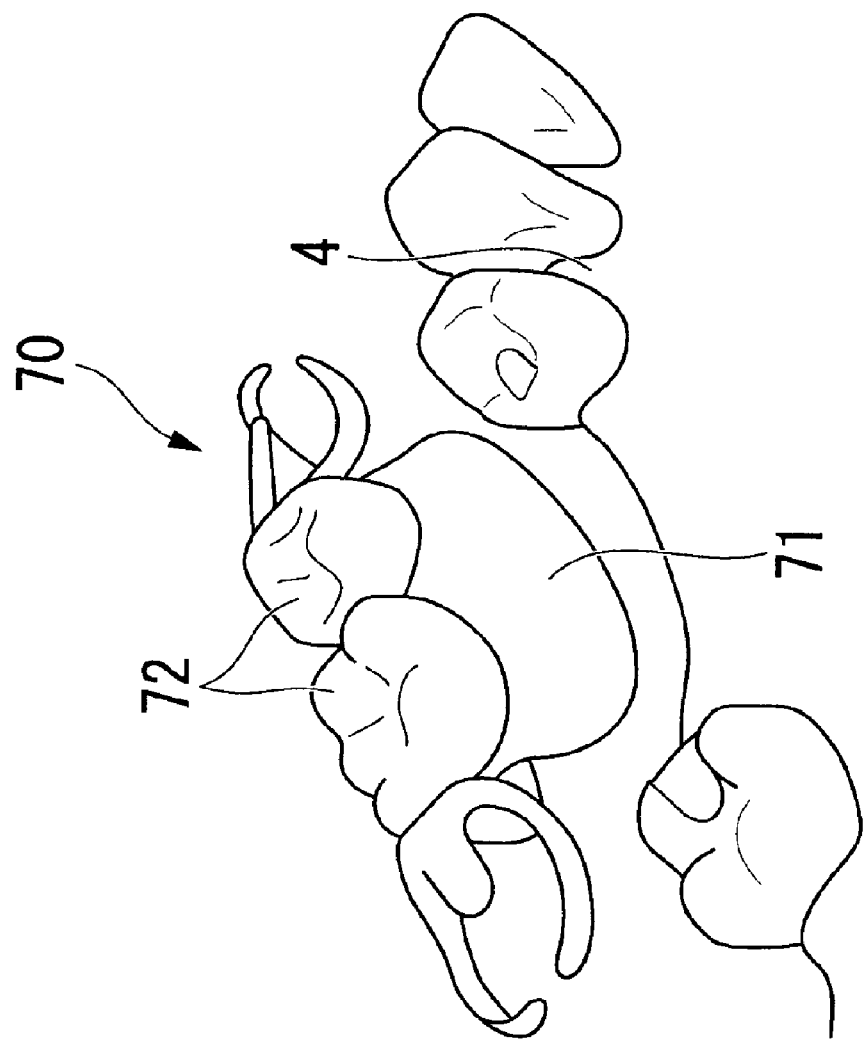
FIG. 10 is a diagram showing a plate denture 70 according to the embodiment of the present invention.

FIG. 10 is a diagram showing a plate denture 70 according to the embodiment of the present invention.

The prosthesis of the present invention may be a plate denture 70 (dentures). The prosthesis may also be a full denture, or a partial denture.

The plate denture (prosthesis) 70 is composed of a denture base 71 formed of resin, and an artificial tooth 72, and serves as a substitute for a defective natural tooth.

A heat treatment (the third process A3, or the fifth process B5) is also performed in the production process of an artificial tooth 71, after a γ-ray sterilization treatment (the second process A2, or the fourth process B4).

Figure 11:
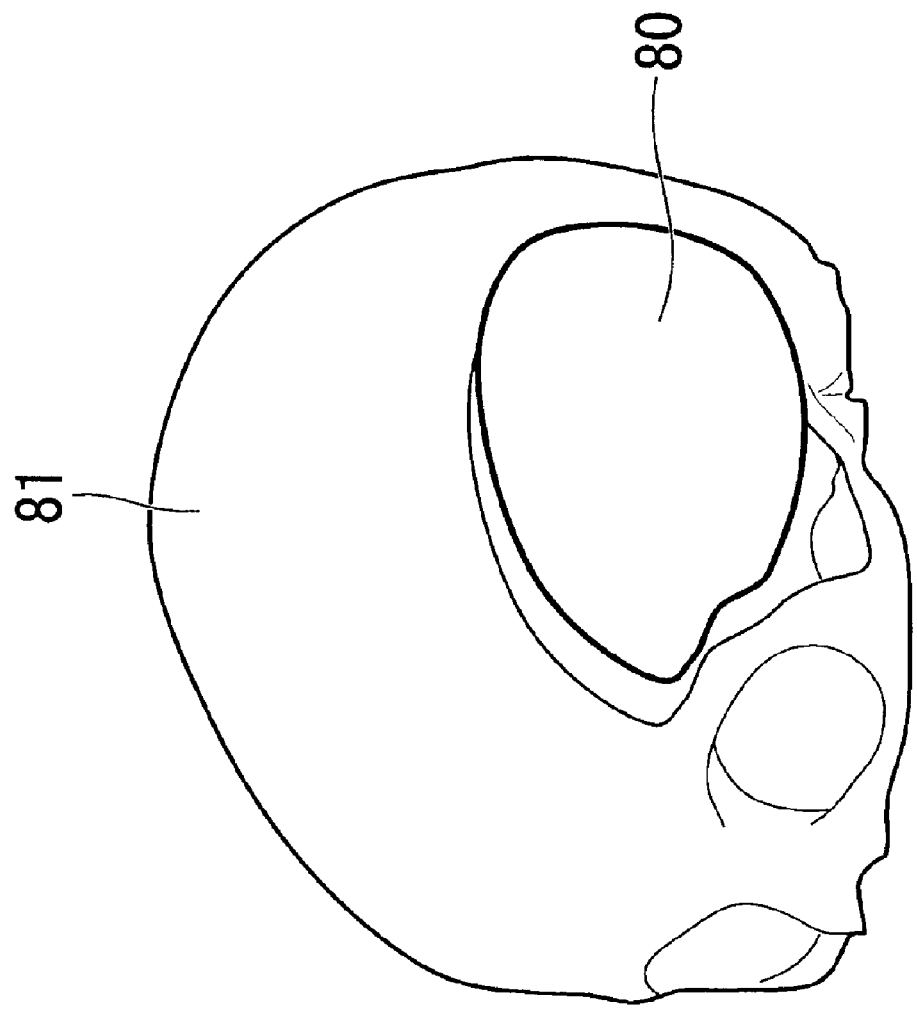
FIG. 11 is a diagram showing an artificial bone 80 according to the embodiment of the present invention.

FIG. 11 is a diagram showing an artificial bone 80 according to the embodiment of the present invention.

The prosthesis of the present invention may be an artificial bone 80. The artificial bone (prosthesis) 80 is, for example, a skull plate, or the like that is arranged on a defective portion of a skull (natural bone) 81.

A heat treatment (the third process A3, or the fifth process B5) is also performed in the production process of an artificial bone 80, after a γ-ray sterilization treatment (the second process A2, or the fourth process B4).

The prosthesis of the present invention is not limited to a case of having a specific shape as in an artificial bone 80. The prosthesis may be a bone prosthetic material (not shown) not having a specific shape.

The prosthesis of the present invention is colored to a color approximate to that of the natural bone without using a coloring material. Therefore, the aesthetics in the oral cavity are not compromised. In the prosthesis of the present invention, a colored material is not used; therefore, there is no adverse effect on the human body.

The technical scope of the present invention should not be limited to the above-described embodiments. Without departing from the gist of the present invention, the present invention also includes ones in which various changes have been added to the above-described embodiments. The specific materials, layer composition, and the like which have been mentioned in the embodiments are only examples, and can be changed appropriately.

The prosthesis of the present invention is formed of a biocompatible ceramic material containing zirconia (zirconium oxide) as a main component. The prosthesis of the present invention may contain zirconia at the volume ratio of 50% or more.

The material of the prosthesis of the present invention may be a zirconia composite material (a combination of zirconia and other ceramic materials). Examples of the other ceramic materials include alumina (aluminum oxide), yttrium oxide, hafnium oxide, silicone oxide, magnesium oxide, and cerium oxide.

The material of the prosthesis of the present invention may be a combination of zirconia and a metal or alloy. Examples of the metal or alloy include copper, titanium, and a titanium alloy.

The material of the prosthesis of the present invention may be a combination of zirconia, carbon, resin, glass, or the like.

A heat treatment (the third process A3, or the fifth process B5) is performed in the production process of the prosthesis of the present invention, after a γ-ray sterilization treatment (the second process A2, or the fourth process B4).

In the forming process (the first processes A1, or B1), an arbitrary production method and an arbitrary apparatus can be used.

In the surface treatment process (the second process B2) and the high temperature heat treatment process (the third process B3), an arbitrary production method and an arbitrary apparatus can be used.

REFERENCE SIGNS LIST

2: alveolar bone (natural bone), 5: dental implant (implant, prosthesis), 6: artificial crown (prosthesis), 8: abutment (prosthesis), 10: fixture (prosthesis), 30: surgical implant (implant, prosthesis), 31: natural bone, 40: filling (prosthesis), 41: natural tooth (natural bone), 50: post crown (prosthesis), 51: tooth root (natural bone), 60: bridge (prosthesis), 70: plate denture (prosthesis), 80: artificial bone (prosthesis), and 81: skull (natural bone)

The invention claimed is:

1. A method for producing a prosthesis containing zirconia and supplementing a defective portion of a natural bone, comprising:
   (1) sintering powder of zirconia to form the prosthesis, and then
   (2) γ-ray sterilizing the prosthesis, which is a formed article containing zirconia, and then
   (3) heat treating the prosthesis, thereby changing a color of the prosthesis a color approximate to that of the natural bone,
   wherein the sintering is performed at a temperature of 1500° C. or more.

2. The method for producing the prosthesis according to claim 1,
   wherein the color approximate to that of the natural bone has the following values in L*a*b* color space:
   L* value of 60 to 90,
   a* value of −5 to 10, and
   b* value of −5 to 10.

3. The method for producing the prosthesis according to claim 1,
   wherein the heat treatment has a highest temperature of 100° C. to 300° C.

4. The method for producing the prosthesis according to claim 1,
   wherein the prosthesis is an implant embedded into and bonded to a natural bone.

5. The method for producing the prosthesis according to claim 4,
wherein the prosthesis is a dental implant.

6. The method for producing the prosthesis according to claim 5,
wherein the prosthesis is a fixture of a dental implant.

7. The method for producing the prosthesis according to claim 5,
wherein the prosthesis is an abutment of a dental implant.

8. The method for producing the prosthesis according to claim 5,
wherein the prosthesis is an implant crown of a dental implant.

9. The method for producing the prosthesis according to claim 1,
wherein the prosthesis is a filling to be embedded into a defective portion of a tooth.

10. The method for producing the prosthesis according to claim 1,
wherein the prosthesis is a post crown to be mounted on a tooth root.

11. The method for producing the prosthesis according to claim 1,
wherein the prosthesis is a bridge composed of an artificial tooth that serves as a substitute for a defective natural tooth, and a crown covering a natural tooth that is to be adjacent to the artificial tooth.

12. The method for producing the prosthesis according to claim 1,
wherein the prosthesis is a plate denture.

13. The method for producing the prosthesis according to claim 1,
wherein the prosthesis is an artificial bone.

14. The method for producing the prosthesis according to claim 1,
wherein the prosthesis is a bone prosthetic material.

15. The method for producing the prosthesis according to claim 1, wherein, in step (2), the γ-ray sterilizing is irradiation performed with a γ-ray in a dose of 25 kGy or more.

16. The method for producing the prosthesis according to claim 1,
wherein the color approximate to that of the natural bone has the following values in L*a*b* color space:
L* value of 65 to 89,
a* value of −2 to 6, and
b* value of −1 to 8.

17. The method for producing the prosthesis according to claim 1,
wherein the method further comprises, prior to step (2):
after sintering the powder of zirconia to form the prosthesis, irradiating the prosthesis with a laser beam, thereby roughening a surface of the prosthesis, and then
heating the prosthesis, thereby whitening the prosthesis.

* * * * *